United States Patent
Segond et al.

(10) Patent No.: US 9,339,521 B2
(45) Date of Patent: May 17, 2016

(54) USE OF VERNONIA EXTRACT

(75) Inventors: Caroline Segond, Labastide-Monrejeau (FR); Alain Loiseau, Bouillon (FR); Virginie Petit, Pau (FR); Eric Theron, Montardon (FR)

(73) Assignee: BAYER CONSUMER CARE AG, Basel (CH)

( * ) Notice: Subject to any disclaimer, the term of this patent is extended or adjusted under 35 U.S.C. 154(b) by 375 days.

(21) Appl. No.: 12/589,026

(22) Filed: Oct. 16, 2009

(65) Prior Publication Data

US 2011/0097429 A1  Apr. 28, 2011

Related U.S. Application Data

(63) Continuation of application No. PCT/EP2008/002689, filed on Apr. 4, 2008.

(30) Foreign Application Priority Data

Apr. 17, 2007  (EP) .................................... 07290472

(51) Int. Cl.
| | | |
|---|---|---|
| *A61K 36/00* | (2006.01) | |
| *A61K 36/28* | (2006.01) | |
| *A61K 8/97* | (2006.01) | |
| *A61Q 19/00* | (2006.01) | |
| *A61Q 19/08* | (2006.01) | |

(52) U.S. Cl.
CPC . *A61K 36/28* (2013.01); *A61K 8/97* (2013.01); *A61Q 19/00* (2013.01); *A61Q 19/08* (2013.01)

(58) Field of Classification Search
None
See application file for complete search history.

(56) References Cited

U.S. PATENT DOCUMENTS

| 7,175,859 | B1 | 2/2007 | Oben | |
|---|---|---|---|---|
| 7,803,409 | B2 | 9/2010 | McClory | |
| 2002/0127256 | A1* | 9/2002 | Murad | 424/401 |
| 2003/0007988 | A1 | 1/2003 | Courtin | |
| 2004/0028643 | A1 | 2/2004 | Chiba | |
| 2009/0123564 | A1 | 5/2009 | Jain | |

FOREIGN PATENT DOCUMENTS

| CN | 1089861 | 7/1994 |
|---|---|---|
| CN | 1141183 | 1/1997 |
| EP | 1854452 | 11/2007 |

OTHER PUBLICATIONS

Manjunatha et al, Evaluation of wound-healing potency of *Vernonia arborea* Hk, Indian Journal of Pharmacology (2005) vol. 37, No. 4, pp. 223-226.*
Johri et al, Medicinal uses of *Vernonia* species, Journal of Medicinal and Aromatic Plant Sceineces 19 (1997) 744-752.*
Ambiaty, Madagascar and Malagasy: ambiaty, accessed on Mar. 30, 2011, pp. 1.*
Rajemisa-Raolison, 1985, Rakibolana Malagasy, Editions Ambozontany, Analamahitsy, Antananarivo, 2003.*
Bezanger-Beauquesne et al, Plant chemistry-polyphenols of *Vernonia pectoralis* Bak. (Compositae), Sciences Naturelles (1975), 281(24), 2025-8.*
Samyn, Jean Marie, "*Vernonia appendiculata*," http://web.archive.org/web/20030719093950/http://hala.refer.mg/imra/plantu/verno.html, 2003.
Leite, S.N. et al., "Wound Healing Activity and Systemic Effect of *Vernonia scorpioides* Extract in Guinea Pig," Fitoterapia, 73 (2002) p. 496-500.
Manjunatha, B. et al., "Evaluation of Wound-Healing Potency of *Vernonia arborea*HK.," Indian J Pharmacol 37 (2005) p. 223-26.
Anonymous, "In-Cosmetics 2007 in Paris," http://web.archive.org/web/20070516152305/http://www.in-cosmetics.com, 2007.
Bayer HealthCare, "New Extract Offical Launch at in Cosmetics 07," XP 00253384, 2011.
Soap Perfumery, "Bayer's Serdes says it with plants," XP 002535385, 2011.
Njoroge, G. et al., "Ethnotherapeutic Management of Skin Diseases Amon the Kikuyus of Central Kenya," J Ethnopharmacology, 111 (2007) p. 303-07.

* cited by examiner

*Primary Examiner* — Qiuwen Mi
(74) *Attorney, Agent, or Firm* — Thomas C. Blankinship

(57) ABSTRACT

The present invention relates to the use of an extract of a *Vernonia* plant from Madagascar in cosmetics, pharmaceuticals and food supplements for improving the skin status, more specifically by strengthening the dermal-epidermal junction and/or by activating fibroblasts synthesis of dermis and extracellular matrix compounds.

6 Claims, 3 Drawing Sheets

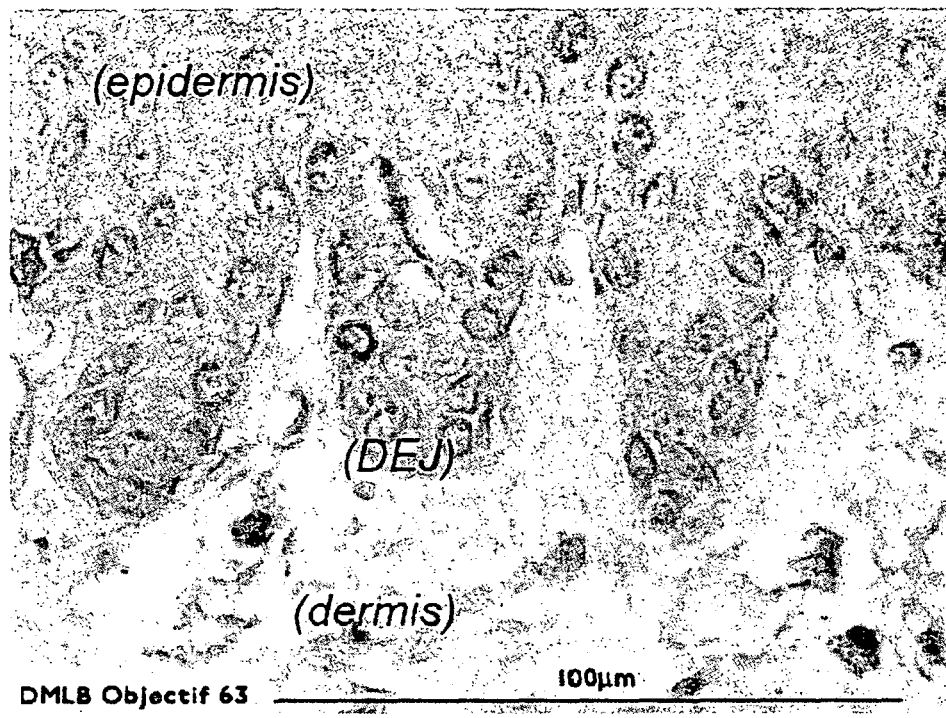
Untreated biopsies
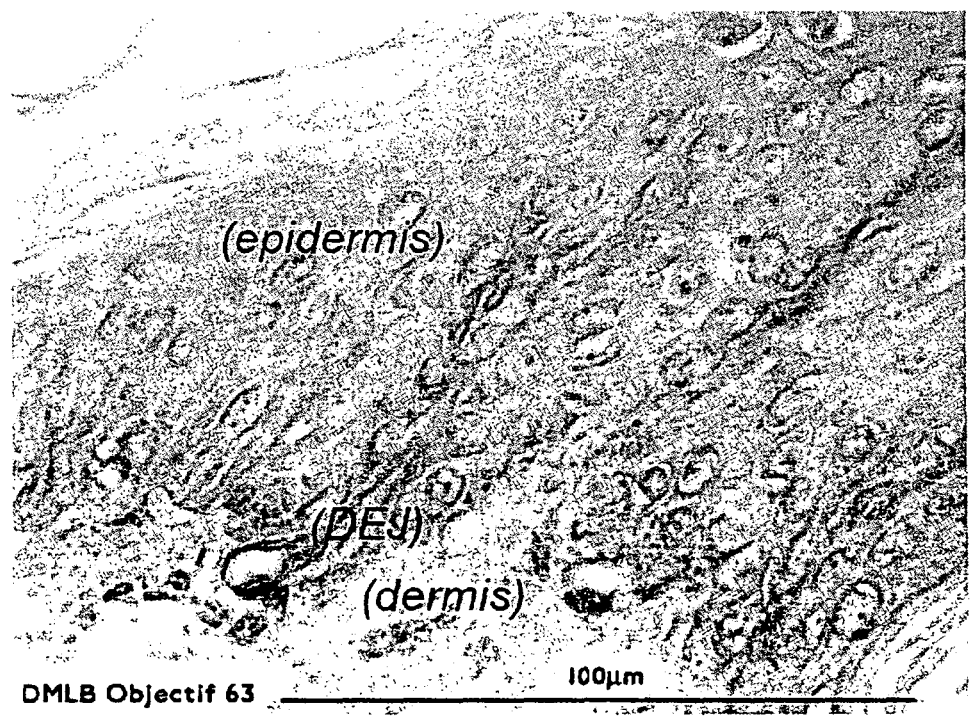
Biopsies treated with Vernonia appendiculata extract
Fig.1: Ex vivo study, GAGs staining at D6

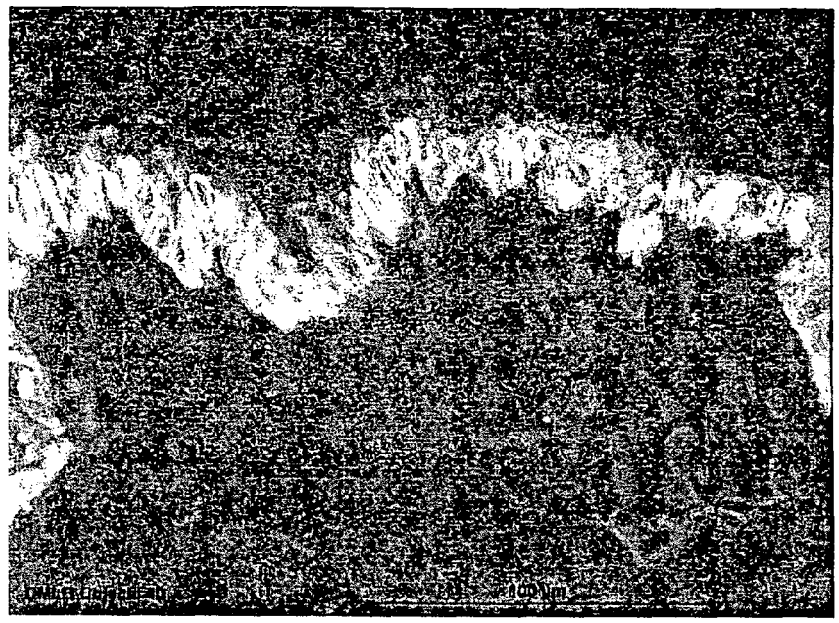
Untreated biopsies
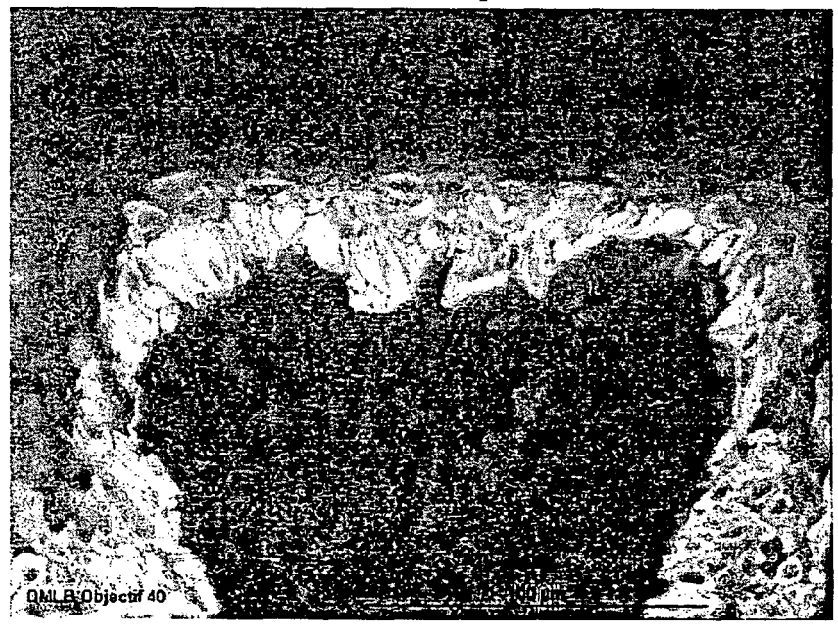
Biopsies treated with Vernonia appendiculata extract
Fig.2: Ex vivo study, Cytokeratine 14 immunomarking at D10

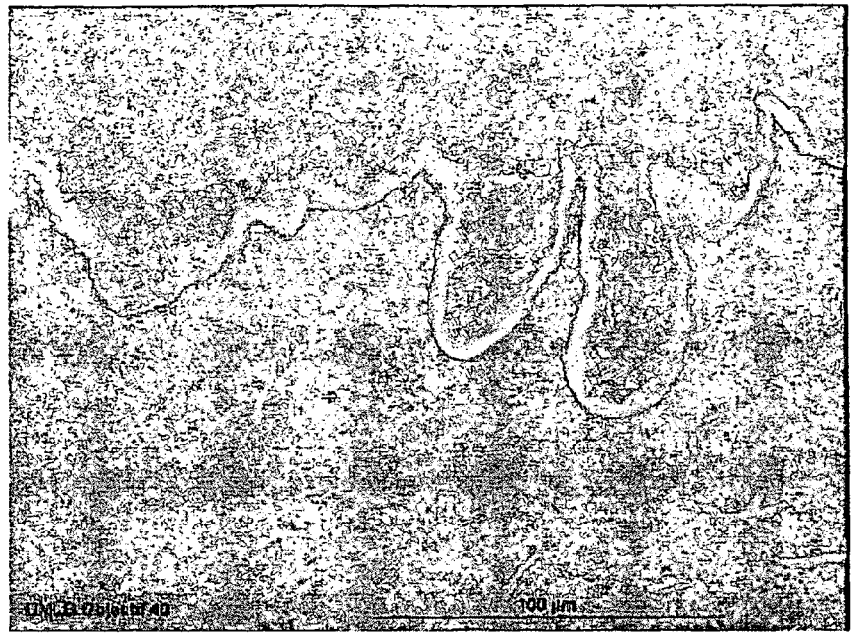
Untreated biopsies
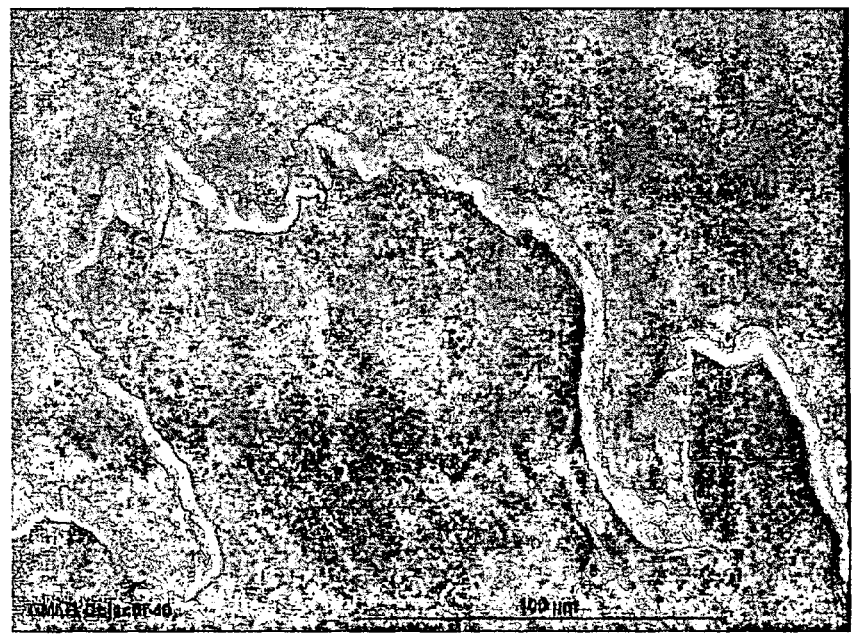
Biopsies treated with Vernonia appendiculata extract
Fig.3: Ex vivo study, Laminin V immunomarking at D10

USE OF VERNONIA EXTRACT

The present invention relates to the use of an extract of a *Vernonia* plant from Madagascar in cosmetics, pharmaceuticals and food supplements for improving the skin status, more specifically by strengthening the dermal-epidermal junction and/or by activating fibroblasts synthesis of dermis and extracellular matrix compounds.

The Vernoniaceae belongs to the Asteraceae (or Compositae) family which is the most important family of the angiosperms as it contains 1600 genus and 22800 species. The genus *Vernonia*, dedicated to W. Vernon, contains 500 to 1000 species widespread in America, Africa and South-East Asia.

*Vernonia appendiculata* can be collected in Madagascar where it is named Ambiaty. This plant is a shrub reaching up to 4 m and is green most of the year but it can become feathery during the dry season. The leaves are alternate with pinnate veins and are grouped at the branch extremity: limb is dentate, hairy, and green on top and white underneath. Blooming gives abundant violet or white flowers and is in September and October. Fruits are akenes with double pappus. In Madagascar, this plant can be found in sunny and dry areas, along rivers and around villages of the High plateaus region (800-1500 m high, topical climate). Ambiaty is traditionally used for e.g. wound healing, antipyretic (malaria), stomach ache, and new leaves can also be cooked as food.

*Vernonia* species are also used for obesity and weight loss (WO 01/15716) and a natriuretic peptide from *Vernonia cinerea* is claimed to have slimming property (WO 01/54659). *Vernonia cinerea* is used for its anti-oxidant property owing to its superoxide dismutase-like and free radicals scavenging activities (EP 1 352 640). *Vernonia anthelmintica* is claimed in oral use for vitiligo treatment with the activation of tyrosinase and the melanin synthesis acceleration (CN1089861, CN1141183). EP 1 854 452 describes extracts of *Vernonia sublutea* for anti-inflammatory use in the dermal and cosmetic field. WO 2007/113851 describes compositions containing active ingredients of *Vernonia* species for treating hair disorders. WO 01/15716 describes a mixture of extracts of plant comprising *Vernonia, Cissus* and *Brillantasia* for controlling weight gain and obesity.

SUMMARY OF THE INVENTION

Chlorogenic acid (3-Caffeoylquinic acid) and isochlorogenic acid (3,5-dicaffeoylquinic acid) are dihydroxycinnamic compounds which are phenolic compounds.

Chlorogenic acid:

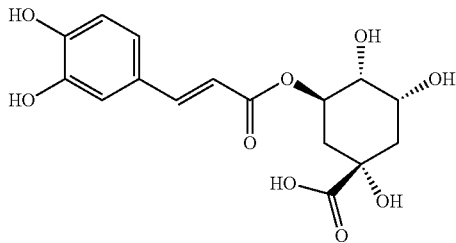

Isochlorogenic acid:

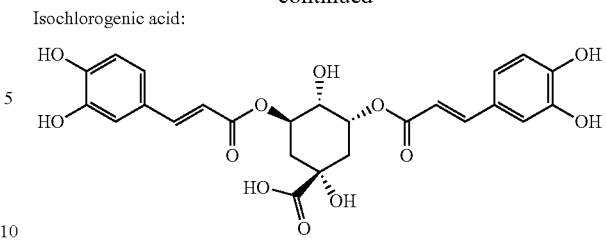

The present invention relates to the use of an extract of a *Vernonia* plant from Madagascar for improving the skin status, more specifically by strengthening the dermal-epidermal junction and/or by activating fibroblasts synthesis of dermis and extracellular matrix compounds.

BRIEF DESCRIPTION OF THE DRAWINGS

FIG. 1 shows a comparison of two biopsies showing GAGs staining at day 6 of an ex vivo study. One sample has been treated with a *Vernonia appendiculata* extract and the other sample is an untreated control.

FIG. 2 shows a comparison of two biopsies showing cytokeratine 14 immuno marking at day 10 of an ex vivo study. One sample has been treated with a *Vernonia appendiculata* extract and the other sample is an untreated control.

FIG. 3 shows a comparison of two biopsies showing laminin V immunomarking at day 10 of an ex vivo study. One sample has been treated with a *Vernonia appendiculata* extract ant the other sample is an untreated control.

The dermal-epidermal junction (DEJ) consists of 2 layers (*Laminae lucida* and *densa*) and multiple connections: this original organization leads to the typical DEJ functions.

DEJ is first a support for the epidermis: basal keratinocytes are linked to the *Lamina lucida* (upper DEJ part) thanks to their hemidesmosomes and the Cytokeratin 14 protein anchoring the keratinocytes actin cytoskeleton in the *Lamina lucida* layer.

DEJ also structures skin as the Collagen IV high content of the *Lamina densa* participates to the mechanical resistance with the typical rete ridge pattern increasing the exchanges surface between epidermis and dermis.

DEJ participates to skin communication, for example with the solute supply and filtration in the *Lamina reticularia* (which is also called reticular dermis and is in fact the upper part of the papillar dermis and is characterized by high cells and vessels contents).

DEJ is essential for skin cohesion between epidermis and dermis, notably with the Laminin V glycoprotein (cohesion filament distributed throughout *L. lucida* and *L. densa*) or with the Collagen VII (curved fibrils inserting into the *L. densa* and extending through the papillar dermis).

Extracts of the present invention can be used for improvement of the status of the skin e.g. by strengthening the dermal-epidermal junction and/or by activating fibroblasts synthesis of dermis and extracellular matrix compounds. That can be achieved e.g. by activation of laminin V synthesis, activation of collagen IV synthesis, activation of cytokeratin 14 synthesis or activation of glucosaminoglycans synthesis. Therefore compounds, mixtures, and extracts of the present invention can also be used for skin anti-aging, densifying and firming of the skin, skin radiance, improvement of the dermal-epidermis junction cohesion, improvement of the skin structuring, a preserved functional interface between epidermis and dermis (communication, nutrition . . . ), the circulation of vital elements, the skin humidity content, the fibroblasts mobility and/or the fibres distribution in the dermis network.

Furthermore the extracts of the present invention can be used for treating RDEB (recessive dystrophic epidermolysis bullosa), sub-epidermic dermatosis bullosa, pemphigoides (bullosa, etc), erythemateous lupus as well as wound healing, ECM renewal, fibrolysis treatment and treatment of the fibrous reticulation (glycation, etc.)

The use of *Vernonia* extract is an appropriate and safe method for the treatment of the skin.

*Vernonia* extracts according to the invention are extracts of plants of the *Vernonia* family from Madagascar which include but are not limited to *Vernonia appendiculata, Vernonia chapelieri, Vernonia diversifolia, Vernonia sublutea, Vernonia trinervis, Vernonia trichoderma, Vernonia pectoralis, Vernonia moquinoides* and *Vernonia eryophylla*. Preference is given to *Vernonia appendiculata*.

The extraction can be performed on all parts of the plant(s). Preferably the leaves of *Vernonia appendiculata* are extracted.

The extraction can be done by standard extraction methods. Preferably the extraction is carried out with a polar solvent applicable for extraction. Leaves are first extracted with a polar solvent optionally by several times. The obtained solution is then mixed and extracted with a non polar solvent e.g. heptan to remove the waxes, essential oils, pigments and most of the non polar molecules. After phase separation, glycerin is added to the aqueous solution in order to adjust the vegetal extract content at a minimum of 10% by weight of the dried extract in a glycerin-water blend 1:1.

An extract according to the invention is normally an extract in solution. Nevertheless the extract can also be used as a dried extract (e.g. after freeze-drying) or be further used in encapsulation process.

The polar solvent used for extraction is preferably alcohol or a mixture of water and alcohol wherein the alcohol is preferably ethanol. The ratio of the volume between water and alcohol can be from 50:50 up to 90:10, preferably 70:30.

The dry plant extract can contain chlorogenic and/or isochlorogenic acids in a total amount of more than 5% by weight of the total extract, or a solution thereof. Most preferably the plant extract is an extract of *Vernonia appendiculata*.

Extracts of the present invention can be administered in any form by any effective route, including, e.g., oral, parenteral, enteral, intravenous, intraperitoneal, topical, transdermal (e.g., using any standard patch), ophthalmic, nasally, local, non-oral, such as aerosal, inhalation, subcutaneous, intramuscular, buccal, sublingual, rectal, vaginal, intra-arterial, and intrathecal, etc. They can be administered alone, or in combination with any ingredient(s), active or inactive. Preference is given to a topical administration.

Extracts of the present invention can be converted in a known manner into the usual formulations such as cosmetic or pharmaceutical compositions or compositions used as food supplement. These may be liquid or solid formulations e.g. without limitation normal and enteric coated tablets, capsules, pills, powders, granules, elixirs, tinctures, solution, suspensions, suppositories, syrups, solid and liquid aerosols, emulsions, pastes, creams, ointments, milks, gels, salves, serums, foams, shampoos, sticks or lotions.

Preference is given to a cosmetic composition in a form of an aqueous solution, a white or colored cream, ointment, milk, gel, salve, serum, foam, shampoo, stick, cream, paste, or lotion.

Extracts of the present invention can be further combined with any other suitable additive or pharmaceutically acceptable carrier. Such additives include any of the substances already mentioned, as well as any of those used conventionally, such as those described in *Remington: The Science and Practice of Pharmacy* (Gennaro and Gennaro, eds, 20th edition, Lippincott Williams & Wilkins, 2000); *Theory and Practice of Industrial Pharmacy* (Lachman et al., eds., 3rd edition, Lippincott Williams & Wilkins, 1986); *Encyclopedia of Pharmaceutical Technology* (Swarbrick and Boylan, eds., 2nd edition, Marcel Dekker, 2002). These can be referred to herein as "pharmaceutically or cosmetically acceptable carriers" to indicate they are combined with the active drug and can be administered safely to a subject for therapeutic purposes.

The dosage of the extracts of the present invention can be selected with reference to the other and/or the type of disease and/or the disease status in order to provide the desired therapeutic activity. These amounts can be determined routinely for a particular patient, where various parameters are utilized to select the appropriate dosage (e.g., type of disease, age of patient, disease status, patient health, weight, etc.), or the amounts can be relatively standard.

The amount of the administered extract can vary widely according to such considerations as the particular compound and dosage unit employed, the mode and time of administration, the period of treatment, the age, sex, and general condition of the patient treated, the nature and extent of the condition treated, the rate of drug metabolism and excretion, the potential drug combinations and drug-drug interactions, and the like.

Preference is given to a composition comprising the dried extract of the present invention in an amount of from 0.01% to 5%, preferably 0.1 to 1% by weight of the total composition.

Preference is also given to a composition containing a solution, preferably a water-based solution, of the extract according to the invention in an amount of from 0.1% up to 10%, preferably 1% up to 7% by weight of the total composition.

The composition according to the invention is administered one or more, preferably up to three, more preferably up to two times per day. Preference is given to a topical administration.

Nevertheless, it may in some cases be advantageous to deviate from the amounts specified, depending on body weight, individual behaviour toward the active ingredient, type of preparation and time or interval over which the administration is effected. For instance, less than the aforementioned minimum amounts may be sufficient in some cases, while the upper limit specified has to be exceeded in other cases. In the case of administration of relatively large amounts, it may be advisable to divide these into several individual doses over the day.

Extracts of the present invention can also be combined with at least one further active substance or plant extract e.g. substances or plant extracts usually employed for dermatological or cosmetic use.

Further active substances include but are not limited to desquamating and/or moisturizing agents, UV filtering or blocking agents, depigmenting or propigmenting agents, antiglycation agents, anti-inflammatory agents, anti-microbial agents, agents stimulating the synthesis of dermal, epidermal, hair or nail macromolecules and/or preventing the degradation thereof, agents stimulating the differentiation of keratinocytes, muscle relaxants, antipollution and/or anti-free radical agents, slimming agents, agents acting on the microcirculation, agents acting on the energy metabolism of the cells, tightening agents, agents preventing the loss or stimulating the growth of hair, agents preventing grey or white hair, or a mixture thereof. Preferably that combination is contained in a topically dermatological or cosmetically composition.

EXAMPLES

Example 1

*Vernonia appendiculata* Extract

Dried leaves of *Vernonia appendiculata* are first extracted with heptan before percolation with ethanol. Fat removal is then obtained thanks to a liquid-liquid extraction with heptan. After concentration into the aqueous phase, glycerine is added to adjust the solution to 10% w/v of vegetal extract in a water-glycerin blend. The final product is then a liquid form.

The composition can be tested by HPLC and a typical composition of the (dried) vegetal extract contains more than 5% of chlorogenic and isochlorogenic acids by weight of the total extract.

Example 2

Anti-Aging Cream

| INCI Name | Amount |
|---|---|
| Glyceryl Stearate (and) PEG-100 Stearate | 2.00 |
| Cetearyl alcohol (and) Cetearyl glucoside | 3.00 |
| Octyldodecyl Myristate | 4.00 |
| Vegetable Squalane | 3.00 |
| Dicaprylyl Ether | 3.00 |
| C8/C10 Triglycerides | 2.00 |
| Cyclomethicone | 3.00 |
| Phenoxyethanol (and) Methylparaben (and) Ethylparaben (and) Propylparaben (and) Isobutylparaben | 0.80 |
| Glycerin | 1.50 |
| Ethoxydiglycol | 0.75 |
| Water (and) Glycerin (and) *Vernonia Appendiculata* Leaf Extract (*Vernonia* extract according to example 1) | 1.00 |
| Water | Qs 100% |

Example 3

Ex Vivo Evaluation of Glucosaminoglycans, Cytokeratine 14 and Laminin V Activation Biopsies from abdominal plastic surgery are used in this ex vivo experiment. They are cultured in a specific survival explants medium: BEM (BIO-EC's Explants Medium).

2 mg of a formulation containing 7% of the extract according to example 1 is applied on the skin stripes at the following times: Day D0, D1, D2, D4, D6 and D8. The results are compared with the untreated skin stripes.

Histological studies are performed at D6 and D10. For morphological analysis, explants are fixed after dehydration and paraffin impregnation, with Bouin's solution. They are then cut and stained by Masson's trichome stain. Specific staining and immunomarking are performed on frozen cryostat cut tissues.

a—Evaluation of Glucosaminoglycans (GAGs):

Specific immunostaining of GAGs is performed by Mowry staining method (Alcian blue stain) and enables to visualize the GAGs present in the papillar dermis and along the dermal-epidermal junction (DEJ) due to pink-violet staining.

Observations of the GAGs at D6:

For all the biopsies, there is no activation of the acid GAGs present in the papillar dermis. Concerning the untreated skin stripes, neutral GAGs are present along the DEJ with moderate staining on an irregular and thin band. For the explants treated with *Vernonia appendiculata* extract, neutral GAGs are clearly marked along the DEJ and form a regular and thin band (FIG. 1).

The amplified marking indicates that the treatment with *Vernonia appendiculata* extract increases the GAGs content in the dermis.

b—Evaluation of Cytokeratin 14:

Specific immunomarking of Cytokeratin 14 is performed thanks to monoclonal antibodies Anti-Keratin 14 (Progen ref RCK107) and revealed by FITC. Cells nuclei are then stained with propodium iodide. Keratin 14 can then be observed in the dermal-epidermal junction area due to fluorescent marking.

Observations of the Cytokeratin 14 at D10:

Concerning the untreated skin stripes, the marking is clear and more and less regular on the basal keratinocytes layer. It is light on the second cells layer. For the explants treated with *Vernonia appendiculata* extract, the marking is very clear and regular on the basal keratinocytes layer and moderate on the second cells layer (FIG. 2).

The treatment with *Vernonia appendiculata* extract helps to upregulate the Cytokeratin 14 release in the epidermis.

c—Evaluation of Laminin V:

Specific immunomarking of Laminin V is performed thanks to monoclonal antibodies Anti-Laminin V (Santa Cruz ref sc 13587) and revealed by FITC. Cells nuclei are then stained with propodium iodide. Laminin V can then be observed in the dermal-epidermal junction area due to fluorescent marking.

Observations of the Laminin V Synthesis:

Whereas the marking is quite clear and more and less regular on the cells membrane for the untreated biopsies, it is very clear and very regular after treatment with *Vernonia appendiculata* extract (FIG. 3).

The treatment with *Vernonia appendiculata* extract helps to upregulate the Laminin V content.

Example 4

Ex Vivo Evaluation of Collagen IV Activation

Biopsies from abdominal plastic surgery are used in this ex vivo experiment. They are cultured in a specific survival explants medium: BEM (BIO-EC's Explants Medium).

2 mg of a formulation containing 1% of the extract according to example 1 is applied on the skin punches at the following times: Day D0, D1, D2, D4, D6 and D8. The results are compared to a control formulation (excipient without active compounds) and to a reference formulation (commercial formulation containing retinol).

Histological studies are performed at D6 and D10.

For morphological analysis, explants are fixed after dehydration and paraffin impregnation, with Bouin's solution. They are then cut and stained by Masson's trichome.

Specific immunomarking of Collagen IV is performed on frozen cryostat cut tissues thanks to monoclonal antibodies Anti-Collagen IV (SBA) and revealed by FITC. Cells nuclei are then stained with propodium iodide. Collagen N can then be observed in the dermal-epidermal junction area and in the upper papillar dermis due to fluorescent marking.

Collagen IV Evaluation by Image Analysis

Image analysis is performed after image digitization and evaluates the surface occupied by the staining. The percentage of the surface occupied by collagen IV is greater for the biopsies treated with *Vernonia appendiculata* extract than for the untreated excised skin or those treated with the excipient: +23.4% versus excipient, +24.8% versus untreated. These values are comparable to the results obtained with a retinol formulation.

What is claimed is:

1. A method for treating a skin disorder comprising the step of topically applying to said skin a formulation comprising an extract of *Vernonia appendiculata* leaves in an amount from about 0.01% to about 5% by weight of the total formulation, and at least one cosmetically or pharmaceutically acceptable carrier, wherein said disorder is selected from the group consisting of recessive dystrophic epidermolysis bullosa, subepidermic dermatosis bullosa, pemphigoides, lupus erythematosus, fibrolysis and fibrous reticulation.

2. The method of claim 1, wherein said extract of *Vernonia appendiculata* leaves is obtained by extraction of raw *Vernonia appendiculata* leaves with a polar solvent selected from the group consisting of alcohol or a mixture of water and alcohol.

3. The method of claim 2, wherein said extract comprises at least 5% by weight of chlorogenic and isochlorogenic acids by weight of the total extract.

4. A method for producing an anti-aging effect on skin, comprising the step of topically administering to said skin a formulation comprising an extract of *Vernonia appendiculata* leaves to an amount from about 0.01% to about 5% by weight of the total formulation, and at least one cosmetically or pharmaceutically acceptable carrier or additive, whereby the formulation produces an anti-aging effect on said skin selected from the group consisting of densifying said skin, firming said skin, strengthening the dermal-epidermal junction in said skin, improving the radiance of said skin; improving restructuring of said skin; preserving a functional interface between the epidermis and dermis of said skin; and improving the humidity content of said skin.

5. The method of claim 4, wherein said leaf extract of *Vernonia appendiculata* is obtained by extraction of raw leaves with a polar solvent selected from the group consisting of alcohol or a mixture of water and alcohol.

6. The method of claim 5, wherein said leaf extract comprises at least 5% by weight of chlorogenic and isochlorogenic acids by weight of the total extract.

* * * * *